United States Patent [19]
Nielsen et al.

[11] Patent Number: 5,968,887
[45] Date of Patent: *Oct. 19, 1999

[54] BORONIC ACID OR BORINIC ACID DERIVATIVES AS ENZYME STABILIZERS

[75] Inventors: Lone Kierstein Nielsen, Lyngby, Denmark; Allison Deane-Wray, Liss, United Kingdom

[73] Assignee: Novo Nordisk A/S, Bagsvaerd, Denmark

[ * ] Notice: This patent is subject to a terminal disclaimer.

[21] Appl. No.: 09/112,483

[22] Filed: Jul. 9, 1998

Related U.S. Application Data

[62] Division of application No. 08/571,954, Jan. 25, 1996, Pat. No. 5,840,677, which is a continuation of application No. PCT/DK94/00249, Jun. 22, 1994.

[30] Foreign Application Priority Data

Jul. 9, 1993 [DK] Denmark .................................. 833/93
Apr. 26, 1994 [DK] Denmark .................................. 477/94

[51] Int. Cl.$^6$ .................................................. C11D 3/386
[52] U.S. Cl. .......................... 510/392; 510/530; 510/468; 510/321; 510/320; 435/188
[58] Field of Search .................................. 510/392, 530, 510/465, 321, 320; 435/188

[56] References Cited

U.S. PATENT DOCUMENTS

| | | | |
|---|---|---|---|
| 5,039,446 | 8/1991 | Estell | 252/174.12 |
| 5,354,491 | 10/1994 | Bjorkquist et al. | 252/135 |
| 5,422,030 | 6/1995 | Pananoike et al. | 252/135 |
| 5,431,842 | 6/1995 | Panandiker et al. | 252/138 |
| 5,472,628 | 12/1995 | Panandiker et al. | 252/135 |
| 5,476,608 | 12/1995 | Boyer et al. | 252/135 |
| 5,488,157 | 1/1996 | Bjorkquist et al. | 562/7 |
| 5,840,677 | 11/1998 | Nielsen et al. | 510/392 |

FOREIGN PATENT DOCUMENTS 0 478 050 A1  9/1991  European Pat. Off. .
WO 92/19707  11/1992  WIPO .

*Primary Examiner*—Kery Fries
*Attorney, Agent, or Firm*—Steve T. Zelson; Carol E. Rozek

[57] ABSTRACT

The invention relates to a liquid composition which comprises an enzyme and a enzyme stabilizing component. The enzyme stabilizing component is a boronic acid derivative.

7 Claims, No Drawings

BORONIC ACID OR BORINIC ACID DERIVATIVES AS ENZYME STABILIZERS

CROSS-REFERENCE TO RELATED APPLICATIONS

This application is divisional application of U.S. application Ser. No. 08/571,954 filed Jan. 25, 1996 now U.S. Pat. No. 5,840,677, which is a continuation of PCT/DK94/00249 filed Jun. 22, 1994 and claims priority under 35 U.S.C. 119 of Danish applications 833/93 and 477/94 filed Jul. 9, 1993 and Apr. 26, 1994, respectively, the contents of which are fully incorporated herein by reference.

FIELD OF INVENTION

This invention relates to a liquid composition containing an enzyme and an improved enzyme stabilizer.

BACKGROUND OF THE INVENTION

Storage stability problems are well known with liquids containing enzyme(s). Especially in enzyme-containing liquid detergents a major problem, in particular if the detergent contains protease, is that of ensuring enzyme activity over time.

The prior art has dealt extensively with improving the storage stability, for example by adding a protease inhibitor.

Boric acid and boronic acids are known to reversibly inhibit proteolytic enzymes. A discussion of the inhibition of one serine protease, subtilisin, by boronic acid is provided in *Molecular & Cellular Biochemistry* 51, 1983, pp. 5–32.

Boronic acids have very different capacities as subtilisin inhibitors. Boronic acids containing only alkyl groups such as methyl, butyl or 2-cyclohexylethyl are poor inhibitors with methylboronic acid as the poorest inhibitor, whereas boronic acids bearing aromatic groups such as phenyl, 4-methoxyphenyl or 3,5-dichlorophenyl are very good inhibitors with 3,5-dichlorophenylboronic acid as a particularly effective one (see Keller et al, *Biochem. Biocphys. Res. Com.* 176, 1991, pp. 401–405).

It is also claimed that aryl boronic acids which have a substitution at the 3-position relative to boron are unexpectedly good reversible protease inhibitors. Especially, acetamidobenzene boronic acid is claimed to be a superior inhibitor of proteolytic enzymes (see WO 92/19707).

The inhibition constant ($K_i$) is ordinarily used as a measure of capacity to inhibit enzyme activity, with a low $K_i$ indicating a more potent inhibitor. However, it has earlier been found that the $K_i$ values of boronic acids do not always tell how effective inhibitors they are (see for instance WO 92/19707).

SUMMARY OF THE INVENTION

In this invention it is surprisingly found that some special boronic and borinic acid derivatives have extraordinary good capacities as enzyme stabilizers.

Accordingly, the present invention relates to a liquid composition comprising an enzyme and a boronic acid or a borinic acid derivative enzyme stabilizer of the following formula:

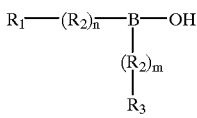

where $R_1$ is an optionally substituted fused aromatic ring structure containing 14 or 18 carbon atoms in the ring, or an optionally substituted monocyclic or fused aromatic heterocyclic ring structure containing up to 17 carbon atoms in the ring, or an optionally substituted monocyclic or fused quinon-oid ring structure containing up to 18 carbon atoms in the ring; $R_2$ has the formula:

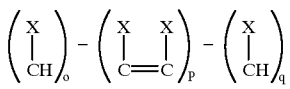

where X is the same or different and selected from hydrogen, $C_1$–$C_6$ alkyl, substituted $C_1$–$C_6$ alkyl, aryl, substituted aryl, hydroxy, hydroxyl derivative, halogen, amine, alkylated amine, amine derivative, nitro, thiol, thiol derivative, aldehyde, acid, acid salt, ester, sulfonate or phosphonate, and o,p and q may be the same or different and may each be 0,1 or 2; m and n may be the same or different and may each be 0 or 1; $R_3$ is the same or different as $R_1$ and selected from $R_1$, or $R_3$ is a hydroxyl group, or $R_1$ and $R_3$ are both optionally substituted monocyclic or dicyclic aromatic ring structures.

In this context optionally substituted ring structures mean that the substituents on the ring structure are freely chosen, but they are preferably selected from hydrogen, $C_1$–$C_6$ alkyl, substituted $C_1$–$C_6$ alkyl, aryl, substituted aryl, hydroxy, hydroxyl derivative, halogen, amine, alkylated amine, amine derivative, nitro, thiol, thiol derivative, aldehyde, acid, acid salt, ester, sulfonate or phosphonate.

DETAILED DISCLOSURE OF THE INVENTION

Preparation of Boronic and Borinic Acid Derivatives

Boronic and borinic acid derivatives may be prepared using methods well known to those skilled in the art, for example by using one of the following methods:

a) Hydroboration of unsaturated materials, i.e. alkenes and alkynes, using either catecholborane (1,3,2-benzodioxaborole) or dichloroborane-dimethyl-sulphide complex as the hydroborating agent, for reference see H. C. Brown, S. K. Gupta in *JACS* 97, 1975, pp. 5249–5255 and H. C. Brown, N. Ravindran, S. U. Kuikarni in *J.Orq.Chem.* 45, (1980), p. 384.

b) The reaction of a Grignard reagent with either tri-n-butylborate or trimethylborate, followed by hydrolysis of the boronic ester thus formed, for reference see F. R. Bean, J. R. Johnson in Jacs 54, 1932, pp. 4415–4425 and S. H. Dandegaonher, S. P. Ingleshwar in *Journal of Shivasi University* 6, 1932, pp. 11–13. Bromo-starting materials that are not commercially available may be prepared conveniently in two steps from the corresponding carboxylic acids by reduction with $LiAlH_4$, followed by treatment with $CBr_4$.

c) The reaction of an organolithium reagent with butylborate, for reference see S. O. Lauesson, pp. 387–395 in *Thionpene Chemistry*, part 7 and D. Florentin, B. Roques in *C.R.Acad.Sc.Paris*, t.270 (May 11, 1970), pp. 1608–1610.

d) Borinic acid derivatives are prepared according to method b. However, the ratio of Grignard reagent to borate adopted is 2:1.

e) Any nuclear substitution or protection of functional groups is achieved by using standard methods well known to those skilled in the art.

Stabilizers

According to the invention the liquid composition may contain up to 500 mM of the stabilizer (the boronic or the borinic acid derivative), preferably the liquid composition may contain 0.001–250 mM of the stabilizer, more preferably the liquid composition may contain 0.005–100 mM of the stabilizer, most preferably the liquid composition may contain 0.01–10 mM of the stabilizer.

Enzymes

According to the invention the liquid composition contains at least one enzyme. The enzyme may be any commercially available enzyme, in particular an enzyme selected from the group consisting of proteases, amylases, lipases, cellulases or peroxidases or any mixture thereof. Mixtures of enzymes from the same class (e.g. lipases) are also included.

The amount of enzyme used in the composition varies according to the type of enzyme(s) and the use intended. If the liquid is a detergent liquid, the amount of each enzyme will typically be 0.2–40 $\mu$M, especially 0.4–20 $\mu$M (generally 5–1000 mg/l, especially 10–500 mg/l) calculated as pure enzyme protein.

Protease: Any protease suitable for use in a liquid composition can be used. Suitable proteases include those of animal, vegetable or microbial origin. Microbial origin is preferred. Chemically or genetically modified mutants are included. It may be a serine protease, preferably an alkaline microbial protease or a trypsin-like protease. Examples of alkaline proteases are subtilisins, especially those derived from Bacillus, e.g. subtilisin Novo, subtilisin Carlsberg, subtilisin 309, subtilisin 147 and subtilisin 168 (described in WO 89/06279). Examples of commercial Bacillus subtilisins are Alcalase®, Savinase®, Esperase® and Durazym™ products of Novo Nordisk A/S. Examples of trypsin-like proteases are trypsin (e.g. of porcine or bovine origin) and the Fusarium protease described in WO 89/06270.

Amylase: Any amylase suitable for use in a liquid composition can be used. Suitable amylases include those of bacterial and fungal origin. Chemically or genetically modified mutants are included. Amylases include, for example, $\alpha$-amylases obtained from a special strain of *B. licheniformis*, described in more detail in British Patent Specification No. 1,296,839. Particularly preferred is Termamyl®, available from Novo Nordisk A/S.

Lipase: Any lipase suitable for use in a liquid composition can be used. Suitable lipases include those of bacterial and fungal origin. Chemically or genetically modified mutants are included. Particularly preferred is lipase obtained by cloning the gene from *Humicola lanuginosa* and expressing the gene in *Aspercillus orvzae*, as described in EP 0 258 068, available under the trade mark Lipolase® from Novo Nordisk A/S.

Cellulase: Any cellulase suitable for use in a liquid composition can be used. Suitable cellulases include those of bacterial and fungal origin. Chemically or genetically modified mutants are included. Suitable cellulases are disclosed in U.S. Pat. No. 4,435,307. Particularly preferred is Celluzyme™ produced by a strain of Humicola insolens, available from Novo Nordisk A/S.

Peroxidase: Any peroxidase suitable for use in a liquid detergent composition can be used herein. Suitable peroxidases herein include those of plant, bacterial and fungal origin. Chemically or genetically modified mutants are included. Examples of suitable peroxidases are those derived from a strain of Coprinus, e.g. *C. cinerius* or *C. macrorhizus*, or from a strain of Bacillus, e.g. *B. pumilus*, particularly peroxidase according to PCT/DK90/00260.

Detergents

If the liquid composition of the invention is a detergent, it will beside enzyme(s) and stabilizer comprise a surfactant.

The liquid detergent may be aqueous, typically containing up to 70% of water and 0–30% of organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be. formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

2) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g PEG, PVP) | 0–3% |
| anchoring polymers as e.g. lauryl metharylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

3) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2–3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

4) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

5) Detergent formulations as described in 1)–4) where the content of linear alkylbenzenesulfonate—or a part of it—is substituted by alkyl sulfate ($C_{12}$–$C_{18}$).

6) Detergent formulations as described in 1)–5) which contain a stabilized or encapsulated peracid either as an additional component or as a substitute for already specified bleach systems.

7) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

Tests of Stabilizers

According to the invention the effectiveness of each stabilizer may be tested in one or more of the following three tests:

a) Storage Stability Test in Liquid Detergent: Enzyme(s) and stabilizer are added to a liquid detergent formulation and stored at well defined conditions. The enzyme activity of each enzyme is determined as a function of time, e.g. after 0, 3, 7 and 14 days.

To calculate the inhibition efficiency from the storage stability date a reaction mechanism is proposed. The following reactions give a relatively simple, but yet plausible, mechanism for a liquid detergent containing protease (P), lipase (L), and inhibitor (I):

I) Autodigestion of protease: $P+P \rightarrow D_P+P$
II) Denaturation of protease: $P \rightarrow D_P$
III) Inhibition of protease: $P+I=PI$
IV) Protease digestion of inhibited enzyme: $P+PI \rightarrow P+D_P+I$
V) Denaturation of inhibited enzyme: $PI \rightarrow D_P+I$
VI) Protease digestion of lipase: $P+L \rightarrow P+D_L$
VII) Denaturation of lipase: $L \rightarrow D_L$ where $D_P$ and $D_L$ are denatured (i.e. non-active) protease and lipase.

From these reactions three coupled differential equations are derived describing the deactivation of P, L and PI. The reaction rate constants are derived from storage stability data by the use of a parameter estimation method (Gauss-Newton with the Levenberg modification). The storage stability data give the concentration of (P+PI) and L as a function of time.

Reaction III is much faster than the other reactions and equilibrium is assumed in the calculations. Reaction IV is excluded from the system to reduce the number of parameters thereby describing the stability of the inhibited enzyme by only one reaction rate constant (from equation V).

In all experiments there is a large surplus of inhibitor molecules compared to protease molecules, i.e. a constant concentration of inhibitor (corresponding to the added amount of inhibitor) is a reasonable assumption.

The specific values of the reaction rate constants are somewhat sensitive to small variations in the data, but the sensitivity is reduced significantly by giving the results relatively to the value from Boric Acid. An improvement factor is thus derived:

$$IF_I = \frac{K_I(\text{Boric Acid})}{K_I(\text{Inhibitor})}$$

$IF_I$ measures the inhibition efficiency given by the inhibition constants $K_I$ from reaction III.

b) The "Milk" Test: In this test the stabilizer to be tested is compared with a reference inhibitor (boric acid). The test is described in details below:

Preparation of "inhibitor" milk: 0.075 g of $CaCl_2$ (dried fine-granular pure, Merck), 0.16 g of 3,3-dimethylglutaric acid (SIGMA) and 2.5 mmole of stabilizer/inhibitor are weighed out and dissolved in 50 ml of demineralised water. pH is adjusted to approx. 6.0 with NaOH. 6.0 g of skimmed milk powder (dehydrated, DIFCO Lab.) are weighed out in a 100 ml beaker, and the solution of salt+buffer+stabilizer/inhibitor is added. This mixture is stirred heavily for some minutes to be sure that all lumps, if any, are apart. Thereafter the mixture is stirred for 30 minutes. pH is adjusted to 6.50 with NaOH. Skimmed milk from a bottle can be used instead of powder. Use milk from the same bottle for all stabilizers/inhibitors in one run.

Preparation of the enzyme: Prepare a solution of approx. 30 KNPU/litre of Savinase® (available from Novo Nordisk A/S) in boric acid buffer (see below). The Savinase activity is determined relatively to an enzyme standard. A folder AF 220/1-GB describing the analytical method of determining the Savinase activity is available upon request to Novo Nordisk A/S, Denmark, which folder is hereby included by reference.

Example: 1.0 g of 16 KNPU/g liquid Savinase is weighed out and 50 ml of boric acid buffer are added. The mixture is stirred for 15 minutes. 10 ml of this solution are filled into a 100 ml beaker, and boric acid buffer is added up to 100 ml. Thereafter the mixture is stirred for 15 minutes. Boric acid buffer: 2.5 g of boric acid (Merck) are dissolved in 500 ml of demineralised water. pH is adjusted to 9.0 with NaOH.

The curdling: 10.0 ml of stabilizer/inhibitor are added to a test tube. 3 test tubes of each stabilizer/inhibitor are made and placed in a 30° C. water bath. The test tubes are left in the water bath for one hour. 1.00 ml of Savinase solution is added to the test tube and the stop-watch is started. The tube is mixed for 10 seconds on the "vibrator" and thereafter placed in the water bath. When the curdling starts the stop-watch is stopped. The deviation between the curdling time for the three test tubes should not be more than approx. 10 seconds. How and when the curdling starts must be learned in practice and the same person should curdle all samples. The curdling time for the reference inhibitor (boric acid) should be around 3–4 minutes (if the curdling time is longer, a stronger protease solution should be used). The curdling time is approx. linear proportional to 1/(protease activity). The result can be reported as an improvement factor IF defined by: (curdling time stabilizer)/(curdling time reference).

c) Determination of $K_i$: The inhibition constant $K_i$ may be determined by using standard methods, for reference see Keller et al, Biochem. Biochys. Res. Com. 176, 1991, pp.401–405; J. Bieth in Baver-Symposium "Proteinase Inhibitors", pp. 463–469, Springer-verlag, 1974 and Lone Kierstein Hansen in "Determination of Specific Activities of Selected Detergent Proteases using Protease Activity, Molecular Weights Kinetic Parameters and Inhibition Kinetics", PhD-report, Novo Nordisk A/S and University of Copenhagen, 1991.

The invention is further illustrated in the following examples which are not intended to be in any way limiting to the scope of the invention as claimed.

EXAMPLE 1

Preparation of 3-Thiopheneboronic Acid

3-Bromothiophene (0.043 m) in sodium dried ether (100 ml) was cooled to −60° C. Butyllithium (30 ml of 1 M) was added rapidly. The mixture was then stirred for 3 minutes, thereafter tri-n-butyl borate (0.043 m) or trimethylborate (0.043 m) in sodium dried ether (25 ml) was added. The mixture was stirred for 4 hours and allowed to warm to room temperature. Thereafter the reaction mixture was treated with hydrochloric acid (1 M) and the ether layer was separated. The aqueous layer was extracted with ether (2 times 25 ml). The combined ether layers were extracted with sodium hydroxide (1 M). The alkaline solution was then acidified with hydrochloric acid (10%), thus precipitating the desired boronic acid. The boronic acid was isolated and then recrystallized from water/ethanol and allowed to dry in air. $C_4H_5BO_2S$, mpt. 163–1640° C.

Preparation of Diphenylborinic Acid.

This was prepared using the above method. The Grignard reagent was prepared from bromobenzene and Magnesium turnings. However, two moles of Grignard reagent were used per one mole of tri-n-butylborate. The borinic acid so formed was isolated by reaction with ethanolamine thus yielding the diphenylborinic acid, ethanolamine complex $((C_6H_5)_2BO \cdot CH_2CH_2NH_2)$, which is easier to handle. Mpt.192–194° C.

EXAMPLE 2

Determination of $K_i$

The inhibition constants $K_i$, for the inhibition of Alcalase and Savinase respectively, were determined using standard methods under the following conditions:

Substrate: Succinyl-Alanine-Alanine-Proline-Phenylalanine-para-nitro-anilide=SAAPFpNA (Sigma S-7388). Buffer: 0.1 M Tris-HCl pH 8.6; 25° C.

Enzyme concentration in assay: Alcalase: $1 \times 10^{-10} - 3 \times 10^{-10}$ M Savinase: $1 \times 10^{-10} - 3 \times 10^{-10}$ M The initial rate of substrate hydrolysis was determined at nine substrate concentrations in the range of 0.01 to 2 mM using a Cobas Fara automated spectrophotometer. The kinetic parameters $V_{max}$ and $K_m$ were determined using ENZFITTER (a non-linear regression data analysis program). $k_{cat}$ was calculated from the equation $V_{max}=k_{cat} \times [E_o]$. The concentration of active enzyme $[E_o]$ was determined by active site titration using tight-binding protein proteinase inhibitors. The inhibition constant $K_i$ was calculated from plots of $K_m/k_{cat}$ as a function of the concentration of inhibitor. The inhibitors were assumed to be 100% pure and the molar concentrations were determined using weighing numbers and molecular weights.

The results of the inhibition constants $K_i$ of the boronic and borinic acid derivative enzyme stabilizers tested are listed below.

TABLE 1

The Inhibition Constants for the Inhibition of Alcalase and Savinase by Different Boronic and Borinic Acid Derivatives Boric Acid are included for Comparison.

| Inhibitor | $K_i$ Alcalase | $K_i$ Savinase |
|---|---|---|
| Boric acid | 30 mM | 20 mM |
| Thiophene-3-boronic acid | 2 mM | 2 mM |
| Thiophene-2-boronic acid | 2 mM | 2 mM |
| 4-Methylthiophene-2-boronic acid | 1.8 mM | 3 mM |
| 5-Ethylthiophene-2-boronic acid | 0.7 mM | 0.9 mM |
| 5-Methylthiophene-2-boronic acid | 2 mM | 3 mM |
| 5-Bromothiophene-2-boronic acid | 0.4 mM | 0.2 mM |
| 5-Chlorothiophene-2-boronic acid | 0.3 mM | 0.2 mM |
| Dibenzothiophene-1-boronic acid | 0.9 mM | 1.5 mM |
| Dibenzofuran-1-boronic acid | 1.1 mM | 1.5 mM |
| Dibenzofuran-4-boronic acid | 0.9 mM | 1.1 mM |
| Picoline-2-boronic acid | 3 mM | 4 mM |
| Diphenylborinic acid (ethanolamine complex) | 2 mM | 4 mM |
| 5-Methoxythiophene-2-boronic acid | 2 mM | 1 mM |
| Thionaphthrene-1-boronic acid | 2 mM | 3 mM |
| Furan-2-boronic acid | 3 mM | 4 mM |
| Furan-3-boronic acid | 10 mM | 7 mM |
| 2,5-dimethyl-thiophene-3-boronic acid | 3 mM | 6 mM |
| Benzofuran-1-boronic acid | 1 mM | 0.8 mM |
| 3-Methoxythiophene-2-boronic acid | 3 mM | 1.2 mM |
| 5-n-Propyl-thiophene-2-boronic acid | 1.5 mM | 3 mM |
| 5-Methoxyfuran-2-boronic acid | 2 mM | 3 mM |
| 3-Bromothiophene-2-boronic acid | 2 mM | 2 mM |
| 5-Ethylfuran-2-boronic acid | 2 mM | 3 mM |
| 4-Carbazole ethyl boronic acid | 1 mM | 2 mM |

EXAMPLE 3
Storage Stability Test in Liquid Detergent

Different boronic and borinic acid derivative enzyme stabilizers were also tested in storage stability tests in liquid detergents using the method described previously under the following conditions:

Detergent Base (US-type) % wt (as pure components)

| | |
|---|---|
| Nansa 1169/p | 10.3 (Linear Alkylbenzene Sulfonate, LAS) |
| Berol 452 | 3.5 (Alkyl Ether Sulfate, AES) |
| Oleic acid | 0.5 |
| Coconut fatty acid | 0.5 |
| Dobanol 25-7 | 6.4 (Alcohol Ethoxylate, AEO) |
| Sodium xylene sulfonate | 5.1 |
| Ethanol | 0.7 |
| MPG | 2.7 (Mono Propylene Glycol) |
| Glycerol | 0.5 |
| Sodium sulfate | 0.4 |
| Sodium carbonate | 2.7 |
| Sodium citrate | 4.4 |
| Citric acid | 1.5 |
| Water | 60.8 |

Enzyme dosage: 1% w/w Saviase (14 KNPU/g)+1% w/w Lipolase (100 KLU/g)

Enzyme Stabilizer Dosage: 5 mmole/kg (for boric acid 160 mmole/kg) Storage: 0, 3, 7 and 14 days at 30° C.

The results of the inhibition effectiveness $IF_I$ of the boronic and borinic acid derivative enzyme stabilizers tested are listed below.

TABLE 2

Different Boronic and Borinic Derivatives Enzyme Stabilizers and the Corresponding $IF_I$. Boric Acid is Included for Comparison.

| Inhibitor | Improvement factor $IF_I$ |
|---|---|
| Boric acid | 1 |
| Thiophene-2-boronic acid | 72 |
| Thiophene-3-boronic acid | 63 |
| 4-Methylthiophene-2-boronic acid | 4 |
| 5-Ethylthiophene-2-boronic acid | 66 |
| 5-Bromothiophene-2-boronic acid | 124 |
| 5-Chlorothiophene-2-boronic acid | 123 |
| Dibenzothiophene-1-boronic acid | 12 |
| Dibenzofuran-1-boronic acid | 9 |
| 5-Methylthiophene-2-boronic acid | 12 |
| 5-Methoxythiophene-2-boronic acid | 14 |
| Furan-2-boronic acid | 13 |
| Dimethylthiophene-3-boronic acid | 7 |
| Furan-3-boronic acid | 32 |
| 3-Methoxythiophene-2-boronic acid | 8 |
| Benzofuran-2-boronic acid | 190 |
| Thionaphthrene-1-boronic acid | 20 |
| Dibenzofuran-4-boronic acid | 19 |

Comparing the results of Table 1 with the results of Table 2 it seems that the effect of a boronic or a borinic acid stabilizer in a detergent can be predicted from the results obtained in buffer systems and vice versa.

We claim:

1. A liquid composition comprising an enzyme and a boronic acid derivative enzyme stabilizer of the following formula:

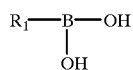

where $R_1$ is:
(a) a substituted fused aromatic ring structure containing 14 or 18 carbon atoms in the ring;
(b) a substituted monocyclic heterocyclic ring structure containing up to 17 carbon atoms in the ring;

(c) a substituted fused aromatic heterocyclic ring structure containing up to 17 carbon atoms in the ring;
(d) a substituted monocyclic quinonone ring structure containing up to 18 carbon atoms in the ring;
(e) a substituted fused quinonoid ring structure containing up to 18 carbon atoms in the ring;
wherein substitutions are selected from the group consisting of hydrogen, $C_1$–$C_6$ alkyl, aryl, hydroxy, halogen, amine, alkylated amine, nitro, thiol, aldehyde, acid, acid salt, ester, sulfonate, and phosphonate.

2. The liquid composition according to claim 1, wherein the enzyme stabilizer is thiophene-2-boronic acid or thiophene-3-boronic acid.

3. The liquid composition according to claim 2, wherein the thiophene group is substituted with bromine or chlorine.

4. The liquid composition according to claim 1, wherein the enzyme stabilizer is 5-bromo-thiophene-2-boronic acid or 5-chloro-thiophene-2-boronic acid.

5. The liquid composition according to claim 2, wherein the thiophene group is substituted with methyl or ethyl.

6. The liquid composition according to claim 5, wherein the enzyme stabilizer is 4-methyl-thiophene-2-boronic acid, 5-methyl-thiophene-2-boronic acid or 5-ethyl-thiophene-2-boronic acid.

7. The liquid composition according to claim 1, wherein the enzyme stabilizer is dibenzothiophene-1-boronic acid.

* * * * *